United States Patent [19]

Ebata et al.

[11] Patent Number: 5,284,973
[45] Date of Patent: Feb. 8, 1994

[54] METHOD OF PREPARING AN ACID ADDITIONAL SALT OF DELTA-AMINOLEVULINIC ACID

[75] Inventors: Takashi Ebata; Hiroshi Kawakami; Katsuya Matsumoto; Koshi Koseki; Hajime Matsushita, all of Yokohama, Japan

[73] Assignee: Japan Tobacco Inc., Tokyo, Japan

[21] Appl. No.: 73,613

[22] Filed: Jun. 8, 1993

Related U.S. Application Data

[63] Continuation of Ser. No. 782,633, Oct. 25, 1991, abandoned.

[30] Foreign Application Priority Data

Oct. 29, 1990 [JP] Japan ................. 2-288481
Feb. 15, 1991 [JP] Japan ................. 3-22372

[51] Int. Cl.$^5$ ......................................... C07C 229/00
[52] U.S. Cl. ................................................. 562/567
[58] Field of Search ..................................... 562/567

[56] References Cited

U.S. PATENT DOCUMENTS 3,846,490 11/1974 Aronova ...................... 562/567
4,325,877 4/1982 Metcalf et al. .

FOREIGN PATENT DOCUMENTS 1358477 7/1974 United Kingdom .

OTHER PUBLICATIONS

Tetrahedron Letters, vol. 25, No. 28, pp. 2977-2980, 1984.
Journal of the Chemical Society, Chemical Communications, vol. 17, pp. 753-754, 1978.
Agric. Biol. Chem., 55(6), 1687-1688, 1991, pp. 1687-1688.
Chem. Abstr., 113:114,653x (1990).

*Primary Examiner*—Michael L. Shippen
*Attorney, Agent, or Firm*—Birch, Stewart, Kolasch & Birch

[57] ABSTRACT

An acid addition salt of δ-aminolevulinic acid is prepared in such a way that tetrahydrofurfurylamine (VI) is reacted with phthalic anhydride under an anhydrous condition to introduce a phthal group which protects amino group of tetrahydrofurfurylamine to give N-tetrahydrofurfuryl phthalimide (III), carbon atoms of the first- and fourth-positions of thus obtained N-tetrahydrofurfurylphthalimide (III) are oxidized at 80° C. using sodium periodate as a oxidizing agent and ruthenium chloride hydrate as a catalyst to yield 5-phthalimidolevulinic acid (II), then the protecting group of 5-phthalimidolevulinic acid (II) is deprotected using an acid to prepare an acid additional salt of δ-aminolevulinic acid. The acid additional salt of δ-aminolevulinic acid is readily converted by neutralization by an alkali to δ-aminolevulinic acid, which is very useful as a precursor of Vitamin B$_{12}$, heme and chlorophyll.

13 Claims, No Drawings

METHOD OF PREPARING AN ACID ADDITIONAL SALT OF DELTA-AMINOLEVULINIC ACID

This application is a continuation, of application Ser. No. 07/782,633 filed on Oct. 25, 1991, now abandoned.

Background of the Invention

1. Field the Invention

The present invention relates to a method of preparing an acid additional salt of δ-aminolevulinic acid. The acid additional salt of δ-aminolevulinic acid is readily converted by neutralization to δ-aminolevulinic acid. δ-aminolevulinic acid is very unstable chemically so that it has been utilized in a form of an acid addition salt generally for storage and transportation.

2. Description of the Related Art

δ-aminolevulinic acid has been known as a precursor of Vitamin $B_{12}$, heme and chlorophyll. Also it has been reported by C. A. Rebaiz et al. of Illinois University, U.S.A. to have a selective herbicidal effect (Enzyme Microb. Technol., Vol. 6, P 390 (1984)).

As methods of preparing an acid additional salt of δ-aminolevulinic acid, which is a synthetic intermediate of δ-aminolevulinic acid, there have been known several methods. For example, L. Pichat et al. have proposed a method of converting δ-bromolevulinate into a δ-phthalimide derivative, and deriving further the derivative to an acid additional salt of δ-aminolevulinic acid (Bull. Soc. Chim. Fr., 1750 (1956)).

S. I. Beale et al. have reported a method of synthesizing an acid addition salt of δ-aminolevulinic acid through a non-enzymic transamination of 4,5-δ-dioxolevulinic acid which is prepared by using δ-bromolevulinic acid as a start material (Phytochemistry, Vol. 18, 441 (1979)).

Further another method has been proposed by A. Pfaltz, wherein an acid additional salt of δ-aminolevulinic acid is synthesized by reducing a keto-nitrile compound in the presence of zinc and acetic acid (Tetrahedoron Lett., Vol. 25, No. 28, 2977 (1984)).

These conventional methods of preparing an acid additional salt of δ-aminolevulinic acid, however, have been suffering from the following drawbacks: none of the above mentioned methods can produce δ-aminolevulinic acid at a high efficiency industrially; the production cost of the acid additional salt is rather high because of the expensive raw material or complicated processes; and further pollusive industrial wastes are yielded.

SUMMARY OF THE INVENTION

The object of the present invention is to provide a method of preparing an acid additional salt of δ-aminolevulinic acid, which salt can be prepared from a cheap and easily available raw material in a high yield.

Another object of the present invention is to provide a method of preparing an acid additional salt of δ-aminolevulinic acid in simple processes nearly free from the pollutive wastes and in an industrially practicable way.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

DETAILED DESCRIPTION OF THE PREFERRED EMBODIMENTS

The present inventors have researched and studied to achieve the objects of the present invention and have found that an acid additional salt of δ-aminolevulinic acid can be prepared by utilizing cheap and readily available tetrahydrofurfurylamine as a starting material through simple processes.

Namely the present inventive is, as shown by the following scheme (I) method of preparing an acid additional salt (I) of δ-aminolevulinic acid comprising:

(a) introducing an amino-protecting group into an amino group of tetrahydrofurfurylamine (IV), thereby obtaining a compound (III);

(b) oxidizing carbon atoms locating at first- and fourth-positions of the obtained compound (III), thereby obtaining a compound (II); and (c) deprotecting the amino-protecting group of the obtained compound (II) by an acid, thereby obtaining the compound (I).

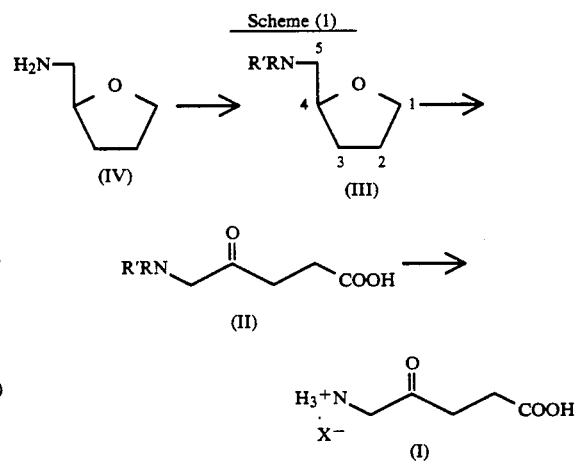

In the scheme (I), R and R' respectively represent a common amino-protecting group or a hydrogen atom and at least one of R and R' is a common amino-protecting group. When both of R and R' are the said amino-protecting group, they may be linked together to form a ring. X represents a monovalent organic or inorganic acid radical.

Herebelow a detail description will be made on the method of preparing an acid additional salt of δ-aminolevulinic acid of the present invention.

In the present invention, cheap and readily available tetrahydrofurfurylamine (IV) will be used as a starting material.

The amino-protecting group in the step (a) may not be particularly restricted so far as it can be commonly employed as an amino-protecting group. For example, acyl groups and siliyl groups may be applicable as the amino-protecting groups. Regarding R and R', both of them may be an amino-protecting groups as described above or either one may be the said amino-protecting group while the other is hydrogen atom. Also R and R' may be an amino-protecting group in which they are connected with each other to form a ring, such as phthalimide.

The oxidation of carbon atoms of first- and fourth-positions in the step (b) can be performed by the oxidizing reaction using ruthenium oxide as a catalyst or the oxidizing reaction using chromic acid series oxidizing agents.

In the oxidation using ruthenium oxide as a catalyst described above, said ruthenium may be e.g., ruthenium tetraoxide, ruthenium dioxide and ruthenium trichloride. The oxidation may be conducted by using such ruthenium oxide with together a strong oxidizing agent, such as, for instance, sodium periodate, potassium periodate, sodium hypochlorite, sodium bromate, etc., in an appropriate solvent at room temperature with stirring over night. The above mentioned appropriate solvent may include e.g., a mixture solvent consisting of carbon tetrachloride, acetonitrile and water, but the present invention may not be limited by this particularly.

While oxidation by chromic acid series oxidizing agents may be performed by using chromic acid series oxidizing agent such as chromium trioxide and t-butyl chromate, etc, in an appropriate solvent, for instance, an organic solvent such as acetone.

The above explained oxidation reactions will proceed via a reaction intermediate (V) as expressed by the following formula. Said reaction intermediate (V) may possibly be isolated during oxidation reaction. The similar oxidation as in the step (b) can be conducted to yield the compound (II) from the reaction intermediate (V).

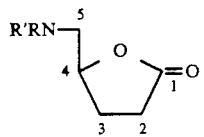
(V)

deprotection reaction in which the amino-protecting group is separated from the compound (II) in the step (c), is carried out in a suitable solvent by using an acid. Acids to be used for the deprotection reaction may be organic or inorganic acid, which reacts with the amino group of δ-aminolevulinic acid to yield an acid addition salt. Examples of such organic acids may e.g., include acetic acid, trifluoroacetic acid and paratoluenesulfonic acid. As inorganic acids, chloric acid, sulfuric acid and nitric acid may be exemplified.

Appropriate solvents to be used in the deprotection reaction may include, for instance, water and dioxane, but the present invention may not be restricted by this particularly.

The acid additional salt of δ-aminovulinic acid (I) thus prepared is neutralized by an alkali such as sodium hydroxide, as disclosed in Unexamined Published Japanese Patent Application No. 2-76841, thereby obtaining δ-aminolevulinic acid.

The present invention will be explained in detail referring to the following Examples.

EXAMPLE 1

(A) Preparation of N-tetrahydrofurfuryl phthalimide 19.8 g (134 mmol) of phthalic anhydride were dissolved in 500 ml of chloroform. To the resultant solution, 10 g (99 mmol) of tetrahydrofurfurylamine were added with stirring. The resultant mixture was subjected to a reflux overnight while the reactant water yielded was distilled off. The thus obtained reaction mixture was allowed to cool and then was poured into 300 ml of aqueous solution of saturated sodium hydrogencarbonate. Thereafter, an organic solvent layer was separated from the reaction mixture. The residual water layer was subjected to an extraction twice with chloroform and the extract thus obtained was combined with the organic solvent layer which was previously separated.

Thereafter, the thus combined organic solvent layer was washed with aqueous solution of sodium hydrogencarbonate and water in order, followed by drying with anhydrous magnesium sulfate. From the thus dried organic solvent layer, the solvent was distilled off under a reduced pressure to obtain crude product. Then the crude product was purified by recrystallization from a mixture solvent of hexane and methylene chloride, thereby forming N-tetrahydrofurfuryl phthalimide. Yield of the product and the properties thereof are as follows:

N-tetrahydrofurfuryl phthalimide
Yield: 21.8 g (yield 95.2%)
Melting point: 86.5°–87.5° C.
$^1$H-NMR(CDCl$_3$) : δ 7.9–7.8 (2H, m, aromatic-H),
7.75–7.65 (2H, m, aromatic-H),
4.3–4.2 (1H, m),
4.0–3.6 (4H, m),
2.1–1.8 (3H, m),
1.75–1.6 (1H, m)

(B) Preparation of 5-phthalimidopentane-4-olide and 5-phthalimidolevulinic acid

To a biphasic solution consisting of 25 ml of carbon tetrachloride, 25 ml of acetonitrile and 30 ml of water, which was dissolving 5.0 g (220 mmol) of N-tetrahydrofurfuryl phthalimide prepared in the above step (A), 19 g (87 mmol) of sodium periodate in the form of powder and 0.10 g (2.2 mol %) of ruthenium chloride hydrate were added, followed by stirring vigorously overnight at an ambient temperature. Upon completion of the reaction, insoluble matter was filtered off. Then the filtrate was subjected to a vacuum distillation to remove the solvent. The thus yielded residue was dissolved by a mixture solution consisting of chloroform and 1N hydrochloric acid aqueous solution, followed by an extraction with chloroform. The organic solvent layer of the extract was dried using anhydrous magnesium sulfate. From the thus dried organic solvent layer, the solvent was distilled off under a reduced pressure thereby, obtaining a residue. The residue was purified by column chromatograpahy on silica gel using a solvent mixture (chloroform:methanol=95:5 v/v) as an eluent, thereby obtaining 5-phthalimidopentane-4-olide. Subsequently using the same column, column chromatography was performed by using another solvent mixture (chloroform:methanol:formic acid=95:4:1 v/v) as an eluent, thereby obtaining 5-phthalimidolevulinic acid. Yields of the thus obtained products and properties thereof are as follows:

5-phthalimidopentan-4-olide
Yield: 1.5 g (yield 28%)
Melting point: 170°–171° C.
$^1$H - NMR (CDCl$_3$) : δ 7.91–7.83 (2H, m, aromatic-H),
7.78–7.72 (2H, m, aromatic-H),
4.87 (1H, dq, J=5.3, 7.1 Hz, H-4)
4.02 (1H, dd, J=14.2, 7.7 Hz, H-5),
3.84 (1H, dd, J=14.2, 5.2 Hz, H-5),
2.71–2.49 (2H, m, H-2),
2.46–2.34 (1H, m, H-3),
2.13–2.03 (1H, m, H-3)

5-phthalimidolevulinic acid

Yield: 2.1 g (yield 37%)
Melting point: 160°-162° C.
$^1$H - NMR (CDCl$_3$ - DMSO - d$_6$): δ 7.88-7.83 (2H, m, aroma
7.78-7.73 (2H, m, aromatic-H),
4.57 (2H, s, H-5),
2.85 (2H, t, J=6.6 Hz, H-3),
2.64 (2H, t, J=6.6 Hz, H-2)

(C) Preparation of 5-phthalimidolevulinic acid

To a biphasic solution consisting of 2.0 ml of carbon tetrachloride, 10 ml of acetonitrile and 3.0 ml of water, which was dissolving 0.30 g (1.2 mmol) of 5-phthalimidopentane-4-olide prepared in the above step (B), 2.5 g (12 mmol) of sodium periodate in the form of powder and 90 mg (30 mol %) of ruthenium chloride hydrate were added, followed by stirring vigorously at 50° C. for 24 hours. Upon completion of the reaction, the reaction mixture was subjected to a vacuum distillation to remove the solvent.

Then the residue thus obtained was dissolved with a solution mixture consisting of chloroform and 1N hydrochloric acid aqueous solution, followed by an extraction with chloroform. The organic solvent layer of the extract was dried anhydrous magnesium sulfate. From the thus dried organic solvent layer, the solvent was distilled off under a reduced pressure, thereby obtaining a residue. The residue was purified by column chromatography on silica gel using a solvent mixture (chloroform:methanol:formic acid=95:4:1 v/v) as an eluent, thereby obtaining 5-phthalimidolevulinic acid. The yield of thus obtained compound and properties thereof are as follows:

5-phthalimidolevulinic acid
Yield: 32 mg (yield 10%)
Melting point: 160°-162° C.
$^1$H - NMR (CDCl$_3$ - DMSO - d$_6$) δ 7.88-7.83 (2H, m, aromatic-H),
7.78-7.73 (2H, m, aromatic-H),
4.57 (2H, s, H-5),
2.85 (2H, t, J=6.6 Hz, H-3),
2.64 (2H, t, J=6.6 Hz, H-2)

(D) Preparation of 5-aminolevulinic acid hydrochloride 2.1 g (8.0 mmol) of 5-phthalimidolevulinic acid prepared in the previous step (B) or (C) were suspended in 100 ml of 6N hydrochloric acid aqueous solution and the resultant was subjected to reflux for 8 hours. Upon completion of the reaction, the reaction solution was cooled to an ambient temperature. After the deposited crystals were filtered off, the filtrate was subjected to a vacuum distillation to remove the solvent, thereby obtaining a residue. The residue was purified by the recrystallization from ethanol-water, thereby forming 5-aminolevulinic acid hydrochloride. Yield of the compound thus prepared and properties thereof are as follows:

5-aminolevulnic acid hydrochloride
Yield: 0.861 g (yield 63.8%)
Melting point: 142°-145° C. (149°-151° C. in the literature)
$^1$H - NMR (D$_2$O) : δ 4.07 (2H, s, H-5),
2.84 (2H, t, J=6.3 Hz, H-3),
2.66 (2H, t, J=6.2 Hz, H-2)

EXAMPLE 2

To a biphasic solution consisting of 2 ml of carbon tetrachloride, 10 ml of acetonitrile and 3 ml of water, which is dissolving 0.30 g (1.3 mmol) of N-tetrahydrofurfuryl phthalimide prepared in the previous step (A) of Example 1, 1.7 g (7.8 mmol) of sodium periodate in the form of powder and 8.0 mg (2.2 mol %) of ruthenium chloride hydrate. The resultant was stirred vigorously overnight at 80° C. Upon completion of the reaction, the reaction mixture was subjected to a vacuum distillation to remove the solvent. The thus obtained residue was dissolved by a solution mixture consisting of chloroform and 1N hydrochloric acid aqueous solution, followed by an extraction with chloroform. The organic solvent layer of the extract was dried using anhydrous magnesium sulfate. From the thus dried organic solvent layer, the solvent was distilled off under a reduced pressure, thereby obtaining a residue. The residue was purified by column chromatography on silica gel using a solvent mixture (chloroform:methanol:formic acid=95:4:1 v/v) as an eluent, thereby obtaining 5-phthalimidolevulinic acid. As a result, 5-phatalimidolevulinic acid can be prepared without 5-phthalimidopropane-4-olide as seen in Example 1. Yield of the compound thus prepared and properties thereof are as follows:

5-phthalimidolevulinic acid
Yield: 0.20 g (yield 59%)
Melting point: 160°-162° C.
$^1$H - NMR (CDCl$_3$ - DMSO - d$_6$) δ 7.88-7.83 (2H, m, aromatic-H),
7.78-7.73 (2H, m, aromatic-H),
4.57 (2H, s, H-5),
2.85 (2H, t, J=6.6 Hz, H-3),
2.64 (2H, t, J=6.6 Hz, H-2)

The amino-protecting group thereof was deprotected as according to the process similar to one as describe in the step (D) of Example 1 to yield 5-aminolevulinic acid hydrochloride, which showed the similar properties as that of Example 1.

From the above results, it was confirmed that 5-aminolevulinic acid hydrochloride can be prepared without forming the reaction intermediate, i.e., 5-phthalimidopentan-4-olide, by the oxidation using ruthenium chloride hydrate at the reaction temperature which is higher than that of Example 1, i.e., 80° C. or more.

Example 3

(A) Preparation of N-benzoyltetrahydrofurfurylamide

To a benzene solution which was dissolving 10 ml (97 mmol) of tetrahydrofurfurylamine and 15 ml (107 mmol) of triethylamine, 11 ml (97 mmol) of benzoyl chloride was added dropwise slowly at 0° C. under anhydrous conditions. Upon completion of the addition, the resultant solution was stirred overnight at an ambient temperature. When the reaction terminated the reaction mixture was subjected to a vacuum distillation to remove the solvent, thereby obtaining a residue. Thereafter the residue was purified by recrystallization from a mixture solvent consisting of n-hexane and ethylacetate, thereby forming N-benzoyltetrahydrofurfurylamide. Yield of thus prepared compound and properties thereof are as follows:

N-benzoyltetrahydrofurfurylamide
Yield: 16 g (yield 77%)
Melting point: 93°-94° C.
$^1$H - NMR (CDCl$_3$) : δ 7.80-7.86 (2H, m, aromatic-H),
7.52-7.38 (2H, m, aromatic-H),
6.61 (1H, br, NH),
4.07 (1H, dq, J=7.1, 3.3 Hz, H-4),
3.93-3.72 (3H, m, H-1, H-5), 3.35 (1H, ddd, J=13.4, 7.7, 5.3 Hz, H-5),
2.09-1.86 (3H, m, H-2, H-3),
1.68-1.54 (1H, m, H-3)

(B) Preparation of 5-benzoylamidopentane-4-olide and 5-benzoylamidolevulinic acid To a biphasic solution consisting of 2 ml of carbon tetrachloride, 10 ml of acetonitrile and 3 ml of water, which was dissolving 0.3 g (1.46 mmol) of N-benzoyl-tetrahydrofurfurylamide prepared in the above step (A), 1.9 g (8.8 mmol) of sodium periodate in the form of powder and 8 mg (2.2 mol %) of ruthenium chloride hydrate. The resultant mixture was stirred vigorously overnight at an ambient temperature. Upon completion of the reaction, insoluble matter in the reaction solution was filtered off. Then the filtrate was subjected to a vacuum distillation to remove the solvent. The thus obtained residue was dissolved by a mixture solution consisting of chloroform and 1N hydrochloric acid aqueous solution, followed by an extraction using chloroform. Subsequently the organic solvent layer of the extract was dried with anhydrous magnesium sulfate. From the thus dried organic solvent layer, chloroform was distilled off under an reduced pressure, thereby obtaining a residue. The residue was purified by column chromatography on silica gel using a solvent mixture (chloroform:methanol=30:1 v/v) as an eluent, thereby obtaining 5-benzoylamidopentane-4-olide. Subsequently using the same column, column chromatography was performed by using an other eluate (chloroform:methanol:formic acid=18:1:1 v/v), thereby obtaining 5-benzoylamidolevulinic acid. Yields of thus prepared compounds and properties thereof are as follows:

5-benzoylamidopentan-4-olide
  Yield: 0.076 g (yield 24.0%)
  Melting point: 129°-130° C.
  $^1$H - NMR (CDCl$_3$) : δ 7.83-7.77 (2H, m, aromatic-H),
  7.54-7.37 (3H, m, aromatic-H),
  7.02 (1H, br, NH),
  4.73 (1H, dq, J=7.3, 3.4 Hz, H-4),
  3.90 (1H, ddd, J=14.5, 6.6, 3.2 Hz, H-5),
  3.54 (1H, ddd, J=14.5, 7.0, 5.6 Hz, H-5),
  2.59-2.51 (2H, m, H-2),
  2.41-2.28 (1H, m, H-3),
  2.09-1.94 (1H, m, H-3)

5-benzolamidolevulinic acid
  Yield 0.075 g (yield 21.8%)
  Melting point: 120°-122° C.
  $^1$H - NMR (CD$_3$OD) : δ 7.85 (2H, d, J=7.1 Hz, aromatic-H),
  7.55 (1H, t, J=7.2 Hz, aromatic-H),
  7.46 (2H, t, J=7.3 Hz, aromatic-H),
  4.26 (2H, s, H-5),
  2.80 (3H, t, J=6.3 Hz, H-3),
  2.61 (2H, t, J=6.4 Hz, H-2)

5-benzolamidopentane-4-olide obtained here was further oxidized in the same way as in the step (C) of Example 1, to give 5-benzoylamidolevulinic acid.

(C) Preparation of 5-aminolevulinic acid hydrochloride 0.874 g (3.72 mmol) of 5-benzolamidolevulinic acid prepared in the step (B) was suspended in 10 ml of 6N hydyrochloric acid aqueous solution and was subjected to a reflux for 7 hours. Upon completion of the reaction, the reaction mixture was cooled to ambient temperature and the deposited crystals were filtered off. Then from the filtrate, the solvent was distilled off under a reduced pressure. Thereafter the residue thus obtained wa purified by recrystallization from hydrous ethanol of 10 wt %, thereby forming 5-aminolevulinic acid hydrochloride. Yield of thus obtained compound and properties thereof are as follows:

5-aminolevulinic acid hydrochloride
  Yield: 0.390 g (yield 62.5%)
  1H - NMR (D$_2$O) : δ 4.07 (2H, s, H-5),
  2.84 (2H, t, J=6.3 Hz, H-3), 2.66(2H, t, J=6.2 Hz, H-2)

Additional advantages and modifications will readily occur to those skilled in the art. Therefore, the invention in its broader aspects is not limited to the specific details shown and described herein. Accordingly, various modifications may be made without departing from the spirit or scope of the general inventive concept as defined by the appended claims and their equivalents.

What is claimed is:

1. A method of preparing an acid additional salt (I) of δ-aminolevulinic acid of the following formula

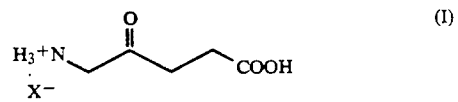

wherein X stands for a monovalent organic or inorganic acid radical, comprising:
(a) introducing an amino-protecting group onto an amino group of a tetrahydrofurfurylamine (IV) of the following formula, thereby obtaining a compound (III) of the following formula:

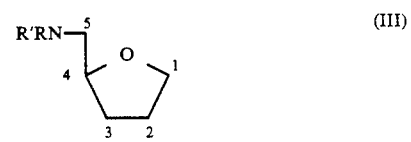

wherein, R and R' respectively represent a common amino-protecting group or a hydrogen atom and at least one of R and R' is the amino-protecting group; when both R and R' are the amino-protecting groups as defined above, R and R' may be linked to each other to form a ring;

(b) oxidizing carbon atoms of the first- and fourth-positions of said compound (III) which is prepared in the above step (a), thereby obtaining a compound (II) of the following formula:

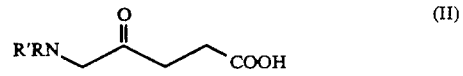

wherein R and R' are the same as described above; and (c) deprotecting said amino-protecting group of said compound (II) which is prepared in said step (b), with an acid, thereby obtaining the compound (I).

2. A method according to claim 1, wherein said amino-protecting group to be introduced into said amino group of tetrahydrofurfurylamine (IV) in said step (a) is an acyl group or a siliyl group.

3. A method according to claim 1, wherein said oxidation of the first- and fourth-position carbon atoms of said compound (III) in said step (b) is conducted in the presence of ruthenium oxide with a strong oxidizing agent.

4. A method according to claim 3, wherein said ruthenium oxide is selected from the group consisting of ruthenium tetraoxide, ruthenium dioxide and ruthenium trichloride.

5. A method according to claim 3, wherein said strong oxidizing agent is selected from the group consisting of sodium periodate, potassium periodate, sodium hypochloride and sodium bromate.

6. A method according to claim 3, wherein said oxidation in said step (b) is performed at a reaction temperature of not lower than 80° C.

7. A method according to claim 1, wherein said oxidation of the first- and fourth-position carbon atoms, of said compound (III) in said step (b) is conducted with a chromic acid series oxidizing agent.

8. A method according to claim 7, wherein said chromic acid series oxidizing agent is selected from the group consisting of chromium trioxide and t-butyl chromate.

9. A method according to claim 1, wherein said acid used for deprotecting said amino-protecting group of said compound (II) in said step (c) is an organic acid.

10. A method according to claim 9, wherein said organic acid is selected from the group consisting of acetic acid, trifluoroacetic acid and paratoluenesulfonic acid.

11. A method according to claim 1, wherein said acid used for deprotecting said amino-protecting group of said compound (II) in said step (c) is an inorganic acid.

12. A method according to claim 11, wherein said inorganic acid is selected from the group consisting of hydrochloric acid, sulfuric acid and nitric acid.

13. A method of preparing an acid additional salt (I) of δ-aminolevulinic acid of the following formula

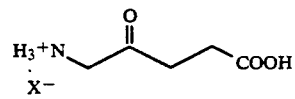

wherein X stands for a monovalent organic or inorganic acid radical, consisting of:

(a) introducing an amino-protecting group onto an amino group of a tetrahydrofurfurylamine (IV) of the following formula, thereby obtaining a compound (III) of the following formula:

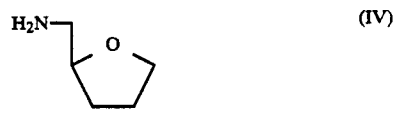

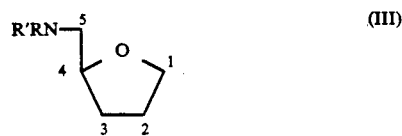

wherein, R and R' respectively represent a common amino-protecting group or a hydrogen atom and at least one of R and R' is the amino-protecting group; when both R and R' are the amino-protecting groups as defined above, R and R' may be linked to each other to form a ring;

(b) oxidizing carbon atoms of the first- and fourth-positions of said compound (III) which is prepared in the above step (a), thereby obtaining a compound (II) of the following formula:

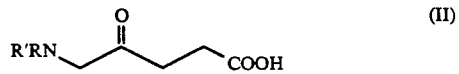

wherein R and R' are the same as described above; and (c) deprotecting said amino-protecting group of said compound (II) which is prepared in said step (b), with an acid, thereby obtaining the compound (I).

* * * * *